United States Patent
Wu et al.

(10) Patent No.: US 9,763,666 B2
(45) Date of Patent: Sep. 19, 2017

(54) LEFT ATRIAL APPENDAGE PLUGGING DEVICE AND DELIVERY SYSTEM

(71) Applicant: APT MEDICAL INC., Xiangxiang (CN)

(72) Inventors: Shulin Wu, Guangzhou (CN); Yuchen Qiu, Xiangxiang (CN); Zhenghui Cheng, Xiangxiang (CN); Xianglong Xiao, Xiangxiang (CN)

(73) Assignee: APT MEDICAL INC., Xiangxiang (CN)

( * ) Notice: Subject to any disclaimer, the term of this patent is extended or adjusted under 35 U.S.C. 154(b) by 0 days.

(21) Appl. No.: 14/419,677

(22) PCT Filed: Oct. 23, 2013

(86) PCT No.: PCT/CN2013/085740
§ 371 (c)(1),
(2) Date: Feb. 5, 2015

(87) PCT Pub. No.: WO2014/127641
PCT Pub. Date: Aug. 28, 2014

(65) Prior Publication Data
US 2015/0342612 A1    Dec. 3, 2015

(30) Foreign Application Priority Data

Feb. 19, 2013   (CN) .......................... 2013 1 0053488
Feb. 19, 2013   (CN) ..................... 2013 2 0077296 U

(51) Int. Cl.
*A61B 17/12*       (2006.01)
*A61B 17/00*       (2006.01)

(52) U.S. Cl.
CPC .. *A61B 17/12122* (2013.01); *A61B 17/12031* (2013.01); *A61B 17/12172* (2013.01);
(Continued)

(58) Field of Classification Search
CPC .... A61B 2017/00623; A61B 17/12022; A61B 17/12122; A61B 17/0057;
(Continued)

(56) References Cited

U.S. PATENT DOCUMENTS 6,152,144 A    11/2000   Lesh et al.
7,122,043 B2   10/2006   Greenhalgh et al.
(Continued)

FOREIGN PATENT DOCUMENTS

CA    2627408 A1    5/2007
CN    1486161 A     3/2004
(Continued)

OTHER PUBLICATIONS

PCT International Search Report dated Feb. 20, 2014 for PCT International Application No. PCT/CN2013/085740, 7 pages.

*Primary Examiner* — Tuan V Nguyen
*Assistant Examiner* — Chima Igboko
(74) *Attorney, Agent, or Firm* — Remarck Law Group PLC

(57) ABSTRACT

A left atrial appendage occlusion device and a delivery system are provided, wherein the left atrial appendage occlusion device includes a stent and an occluder. Firstly, the stent is implanted and fixed at the entrance of the left atrial appendage; then, a double-disc occluder is released on the stent to occlude the left atrial appendage. The left atrial appendage occlusion device includes a self-expandable nitinol stent, which is firmly fixed at the entrance of the left atrial appendage via a two-way anchoring thorn, and then an occluder is released on the stent. The left atrial appendage occlusion device is delivered to the left atrial appendage by the delivery system. Compared with the prior art, the delivery system improves the releasing accuracy and the implanting stability of the occluder. After being released, both the
(Continued)

stent and the occluder can be withdrawn into a catheter to be relocated or replaced.

16 Claims, 5 Drawing Sheets

(52) U.S. Cl.
CPC . *A61B 17/0057* (2013.01); *A61B 2017/00579* (2013.01); *A61B 2017/00592* (2013.01); *A61B 2017/00623* (2013.01); *A61B 2017/00628* (2013.01); *A61B 2017/1205* (2013.01)

(58) Field of Classification Search
CPC A61B 2017/00575; A61B 2017/00579; A61B 2017/00592; A61B 2017/00606; A61B 2017/001615; A61B 17/12118
See application file for complete search history.

(56) References Cited

U.S. PATENT DOCUMENTS

| | | | |
|---|---|---|---|
| 7,648,532 B2 | 1/2010 | Greenhalgh et al. | |
| 7,972,359 B2* | 7/2011 | Kreidler | A61B 17/0057 606/200 |
| 2003/0171739 A1* | 9/2003 | Murphy | A61B 17/12022 606/1 |
| 2004/0220610 A1* | 11/2004 | Kreidler | A61B 17/0057 606/200 |
| 2006/0009799 A1 | 1/2006 | Kleshinski et al. | |
| 2009/0171386 A1 | 7/2009 | Amplatz et al. | |
| 2009/0228038 A1 | 9/2009 | Amin | |
| 2009/0275976 A1 | 11/2009 | Kleshinski et al. | |
| 2012/0071918 A1 | 3/2012 | Amin et al. | |
| 2012/0101571 A1 | 4/2012 | Thambar et al. | |
| 2013/0165967 A1 | 6/2013 | Amin et al. | |

FOREIGN PATENT DOCUMENTS

| | | |
|---|---|---|
| CN | 2613248 | 4/2004 |
| CN | 1711978 A | 12/2005 |
| CN | 1799521 A | 7/2006 |
| CN | 1852688 A | 10/2006 |
| CN | 2904980 | 5/2007 |
| CN | 100394895 | 6/2008 |
| CN | 101304693 A | 11/2008 |
| CN | 101518470 A | 9/2009 |
| CN | 201879866 U | 6/2011 |
| CN | 201899524 U | 7/2011 |
| CN | 202143640 U | 2/2012 |
| CN | 102438546 A | 5/2012 |
| CN | 202335893 U | 7/2012 |
| CN | 102805654 A | 12/2012 |
| CN | 103099652 A | 5/2013 |
| CN | 203226856 U | 10/2013 |
| CN | 102395323 B | 3/2014 |
| WO | 0238051 A2 | 5/2002 |
| WO | 03032818 A2 | 4/2003 |
| WO | 2012091809 A1 | 7/2012 |

* cited by examiner

LEFT ATRIAL APPENDAGE PLUGGING DEVICE AND DELIVERY SYSTEM

This application is the national phase of International Application No. PCT/CN2013/085740, titled "LEFT ATRIAL APPENDAGE PLUGGING DEVICE AND DELIVERY SYSTEM", filed on Oct. 23, 2013, which claims the benefit of priorities to the following Chinese Patent Applications:

1. Chinese Patent Application No. 201310053488.X, titled "LEFT ATRIAL APPENDAGE OCCLUSION DEVICE AND DELIVERY SYSTEM", filed with the Chinese State Intellectual Property Office on Feb. 19, 2013;

2. Chinese Patent Application No. 201320077296.8, titled "LEFT ATRIAL APPENDAGE OCCLUSION DEVICE AND DELIVERY SYSTEM", filed with the Chinese State Intellectual Property Office on Feb. 19, 2013. The entire disclosures of all applications are incorporated herein by reference.

TECHNICAL FIELD

The present application relates to the technical field of medical equipment, and particularly to a left atrial appendage occlusion device and a delivery system.

BACKGROUND

Stroke is a major complication that causes disability or death of patients suffering from atrial fibrillation (AF). As indicated by epidemiological data, about 15 million people worldwide suffer from stroke each year, and 15% to 20% of the strokes are caused by atrial fibrillation. Study suggests that, cardiogenic thrombus of 60% of patients suffering from rheumatic heart disease with atrial fibrillation is from left atrial appendage, and this proportion is larger than 90% in patients suffering from non-valvular heart disease with atrial fibrillation. Therefore, the study of thromboembolic complications of atrial fibrillation has received more and more attention, and prevention and treatment of stroke in patients with atrial fibrillation have great clinical significance.

At present, there are three methods for treating atrial fibrillation, which include surgery, medication and internal medicine intervention. The left atrial appendage is the key to the treatment of atrial fibrillation due to its important role in the thrombosis formation of patients with atrial fibrillation. In the early, surgery is performed to occlude the left atrial appendage, however, this method has disadvantages of large trauma and high risk, thus has not been widely used clinically. Although the effect of preventing the stroke in patients with atrial fibrillation by using anticoagulants has been well received, some patients, particularly elderly patients who have a high incidence of atrial fibrillation, can not benefit from the anticoagulant therapy because of bleeding tendency or contraindications to anticoagulant therapy such as bleeding. At present, the most advanced treatment for preventing thromboembolic complications of atrial fibrillation domestic and overseas is percutaneous left atrial appendage occlusion, which releases a specialized occluder through a catheter to occlude the left atrial appendage, so as to prevent atrial fibrillation fundamentally. This kind of minimal invasive intervention treatment has benefits of short duration, small trauma and more effective, especially for those patients who have contraindications or a high risk of bleeding if taking anticoagulants.

There are considerable limitations in conventional percutaneous left atrial appendage occlusion in which an occluder is positioned into the left atrial appendage by means of catheter intervention. Most of occluders cannot fully fit the anatomic structure of the left atrial appendage because of the left atrial appendage has a complicated anatomic structure and various shapes and depths, thus the occluder is difficult to be stably fixed. The opening and the interior of the left atrial appendage has irregular shape and uneven surface, thus the coating of the occluder may form a number of concave pit-shaped gaps at the opening of the left atrial appendage, and cannot completely occlude the opening of the left atrial appendage, thus the desirable occlusion effect cannot be achieved. Also, in conventional products, a soft anchoring thorn is difficult to stab into the wall of the left atrial appendage, thus cannot be stably fixed, and a hard anchoring thorn has an enough puncture force, but may hinder the recovery, relocation and replacement of the occluder, and may even pierce the left atrial appendage. In addition, since the occluder is located within the left atrial appendage, its support force may expand the left atrial appendage, which may lead to abrasion between the left atrial appendage and the pericardium.

SUMMARY

An object of the present application is to provide a left atrial appendage occlusion system, and the technical issues to be addressed are to release a plum blossom shaped metal stent via a catheter and firmly fix the stent at an entrance of the left atrial appendage, and then to release a double-disc occluder on the stent to completely occlude a passage between the left atrium and the left atrial appendage, thereby preventing stroke resulting from left atrial appendage thrombus caused by atrial fibrillation.

To address the above technical issues, a left atrial appendage occlusion device is provided according to the present application, which includes:

a stent configured to be released and fixed at an entrance of a left atrial appendage to establish an artificial position for fixing an occluder; and an occluder configured to be released and fixed to the stent to occlude the left atrial appendage.

Preferably, the stent is formed by laser-cutting a nickel-titanium alloy tube or heat shaping braided nickel-titanium alloy wires, and is in a shape of plum blossom in a released state, and a plurality of flexible support rods are connected to a hub to form the stent;

the stent is provided with a plurality of two-way anchoring thorns configured to hook a wall of an atrium at the entrance of the left atrial appendage; and the hub is located at a center of the stent; and a metal sleeve, screw threads, a hole, or a hook is provided on the hub to connect the hub with a delivery system.

Preferably, the stent includes the flexible support rods at a periphery of the stent and the hub; and the flexible support rods form a proximal end disk and a distal end disk which has the same shape and structure, and the two disks are respectively connected to two hubs having the same size.

Preferably, support rods at a periphery of each of the two disks of the stent form a regular polygon, and axial support rods are provided at vertexes of the polygons of the two disks to connect the support rods at the peripheries of the two disks.

Preferably, two ends of each of the support rods are both provided with one anchoring thorn, and the anchoring thorn has a length of 1 mm to 3 mm, and has a root arranged on the respective support rod.

Preferably, on the support rod, an indicator is provided or not provided at a middle portion between two anchoring thorns or at the root of each anchoring thorn, and the indicator is made of platinum, gold, platinum alloy, tungsten alloy or gold alloy.

Preferably, the hubs includes a proximal end hub and a distal end hub, and the proximal end hub includes an inner hole provided with screw threads, a hole, or a hook, and the screw threads, the hole, or the hook is configured to be connected to an outer catheter of the delivery system.

Preferably, a metal sleeve is welded in the distal end hub and is made of stainless steel, nickel-titanium alloy, titanium alloy, platinum, or platinum alloy.

Preferably, the metal sleeve is provided with screw threads, a hole, or a hook, and the screw threads, the hole, or the hook is configured to be connected to an inner catheter of the delivery system.

A delivery system for delivering the left atrial appendage occlusion device described above is further provided according to the present application, and includes a distal end outer sheath and a system grip, wherein in a case that the distal end outer sheath is withdrawn and the stent is delivered, the system grip is twisted to control two ends of the stent to retreat to a center of the stent at the same time, or to control two ends of the stent to be stretched outwards at the same time to restore the stent to a retracted state before being released, and the position of the stent is adjusted, then the stent is released again till the stent is accurately fixed at the entrance of the left atrial appendage.

Preferably, the distal end outer sheath is provided on the delivering system or is provided separately, and the distal end outer sheath is slidably connected to the stent.

Preferably, the delivering system is provided with an outer catheter and an inner catheter which are coaxial and are slidable with respect to one another.

Preferably, the outer catheter has a distal end connected to the proximal end hub of the stent, and a connector is provided between the outer catheter and the hub.

Preferably, the inner catheter has a distal end connected to the metal sleeve on the distal end hub of the stent, and a connector is provided between the inner catheter and the metal sleeve.

Preferably, a double-disk occluder is provided to be released and fixed to the stent, and has a proximal end disk located within a left atrium, a distal end disk located within the stent or a left atrial appendage, and a waist passing through the proximal end hub or passing through the proximal end hub and the metal sleeve at the same time.

Preferably, the occluder includes the proximal end disk and the distal end disk, and a polymeric membrane made of polyethylene terephthalate or polytetrafluoroethylene is provided inside the proximal end disk.

Preferably, a diameter of the proximal end disk is greater than a diameter of the stent by 2 mm to 30 mm, and the distal end disk has a diameter of 4 mm to 20 mm.

With the above technical solutions, the present application has the following advantages compared with the conventional technology.

1. During the operation, firstly, the stent is released and fixed to establish an artificial position for fixing the occluder. Then various appropriate types of double-disk occluders are released and fixed to the stent, which provides selectivity.

2. The two two-way anchoring thorns are provided on the axial support rods at the periphery of the stent, thereby ensuring that the stent is fixed firmly at the entrance of the left atrial appendage, and will not move or tilt in two directions. The duration required for releasing and fixing the stent at the entrance of the left atrial appendage is short.

3. After the stent is released, two ends of the stent may be controlled by a catheter to slide symmetrically in opposite directions, which allows the anchoring thorns to be withdrawn to the axial support rods of the stent automatically to adjust the releasing position, or even to withdraw the whole stent into the catheter to relocate and release or replace the stent.

4. The grip of the delivery system may be twisted to control the catheter to drive two ends of the stent to slide symmetrically in opposite directions, thus when releasing the stent, the two-way anchoring thorns of the stent will not move with respect to the left atrial appendage in the axial direction, and the operation is convenient, and facilitates releasing the stent precisely and securely.

5. In this system, an appropriate occluder may be selected according to the clinical situation, and the large-diameter proximal end disk of the occluder may completely cover the entrance of the left atrial appendage, thereby realizing the effect of completely occluding the left atrial appendage.

6. The manner for releasing the occluder on the stent of this left atrial appendage occlusion device will not enlarge the left atrial appendage, thereby avoiding the abrasion between the enlarged left atrial appendage and the pericardium.

BRIEF DESCRIPTION OF THE DRAWINGS

For more clearly illustrating embodiments of the present application or the technical solution in the conventional technology, drawings referred to describe the embodiments or the conventional technology will be briefly described hereinafter. Apparently, the drawings in the following description are only to describe the embodiments in the present application, and for the person skilled in the art, other drawings may be obtained based on the drawings without any creative efforts.

DETAILED DESCRIPTION

Figure 1:
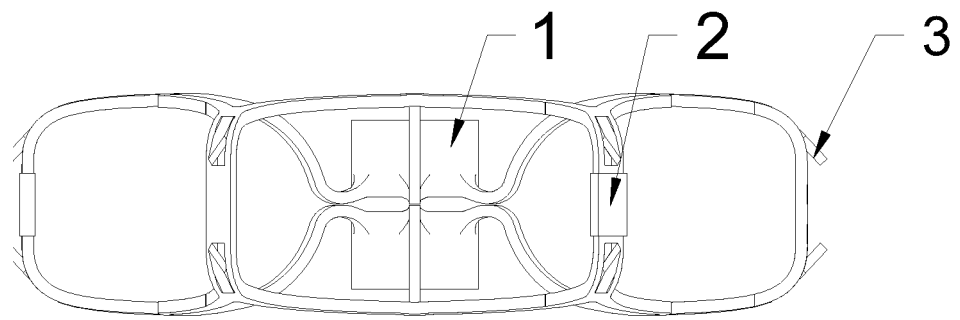
FIG. 1 is a schematic front view showing the structure of a stent according to an embodiment of the present application.
Figure 2:
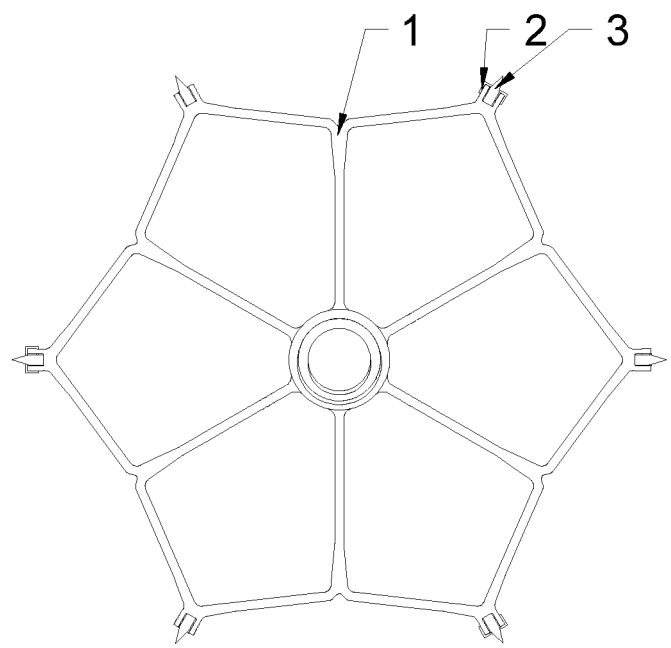
FIG. 2 is a schematic top view showing the structure of the stent according to the embodiment of the present application.
Figure 3:
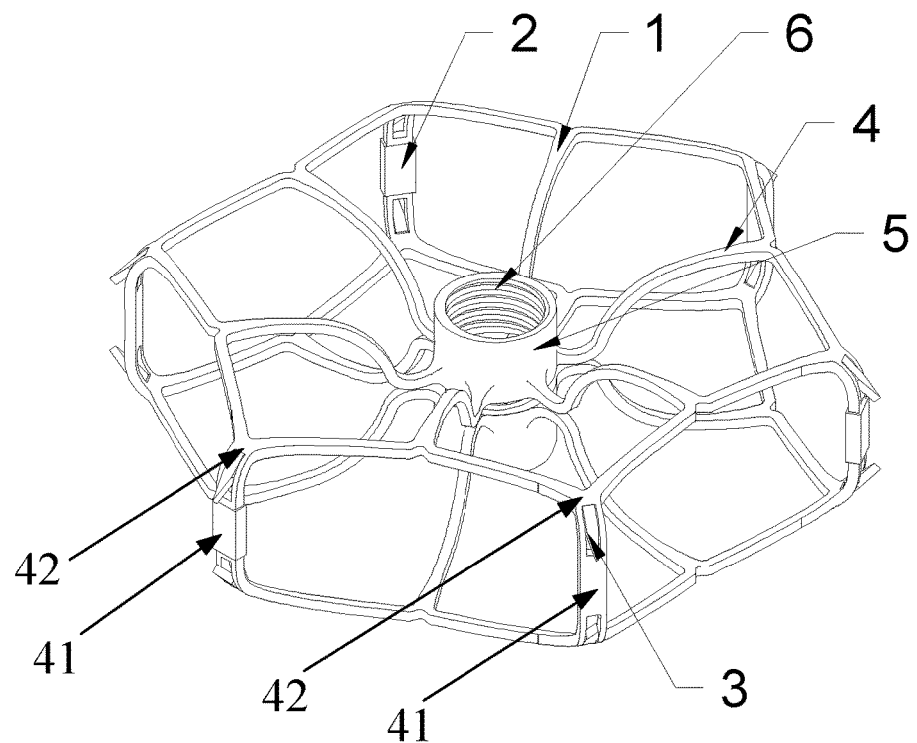
FIG. 3 is an isometric perspective view showing the structure of a proximal end of the stent according to the embodiment of the present application.
Figure 4:
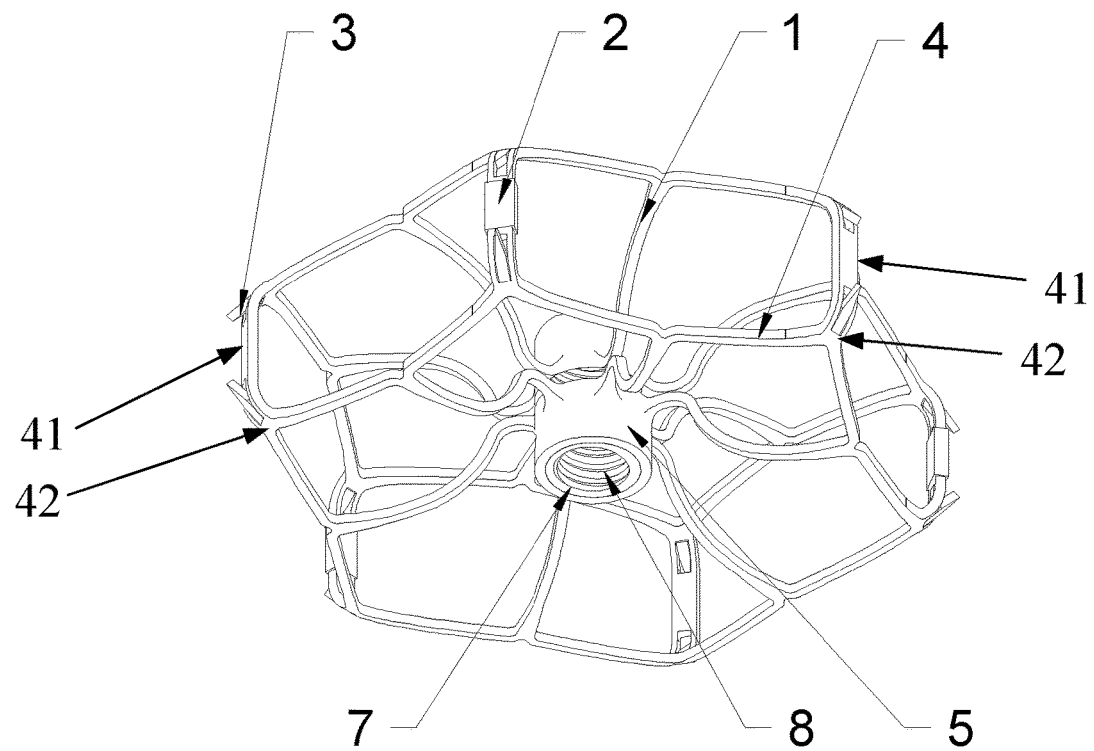
FIG. 4 is an isometric perspective view showing the structure of a distal end of the stent according to the embodiment of the present application.

The present application is further described in detail hereinafter in conjunction with the drawings and the embodiments.

Reference Numerals in the drawings are indicated as follows. 1 refers to a stent for fixing an occluder, 2 refers to an indicator on the stent, 3 refers to an anchoring thorn, 4 refers to a flexible support rod on the stent, 5 refers to a hub, 6 refers to screw threads on hub, 7 refers to a metal sleeve, 8 refers to screw threads on the metal sleeve, 9 refers to a connector of an inner catheter, 10 refers to a twist grip, 11 refers to a safety nut, 12 refers to a fixing grip, 13 refers to a distal outer sheath, 14 refers to an outer catheter of the delivery system, 15 refers to an inner catheter of the delivery system, 16 refers to a connector between the outer catheter and the hub, 17 refers to a connector between the inner catheter and the metal sleeve, 18 refers to an end nut, 19 refers to an occluder, 20 refers to a proximal end disk of the occluder, 21 refers to a polymeric membrane made of PET or PTFE, 22 refers to a waist of the occluder, 23 refers to a distal end disk of the occluder, 24 refers to a tip, 25 refers to a left atrium, and 26 refers to a left atrial appendage.

A left atrial appendage occlusion device and a delivery system according to the present application are provided with a plum blossom shaped self-expandable metal stent. The stent is arranged in the delivery system and is slidably connected to a distal outer sheath, and a double-disk occluder may be released to be fixed to the stent.

As shown in FIGS. 1 to 4, a stent 1 includes a peripheral flexible support rod 4 and a middle hub 5. The stent 1 includes multiple flexible support rods, a proximal end hub 5 and a distal end hub 5, and the proximal end hub 5 and the distal end hub 5 are located at a center of the stent 1. The multiple flexible support rods include peripheral flexible support rods 4 provided at a periphery of the stent 1 and axial flexible support rods 41. The peripheral flexible support rods 4 form a proximal end disk and a distal end disk which has the same shape and structure, and the proximal end disk and the distal end disk of the stent 1 are respectively connected to the proximal end hub 5 and the distal end hub 5, and the proximal end disk and the distal end disk of the stent 1 each forms a regular polygon, and the axial support rods 41 are respectively provided between corresponding vertexes 42 of the regular polygons to connect the proximal end disk and the distal end disk of the stent 1.

Two ends of the axial support rod 41 are respectively provided with an anchoring thorn 3 having a length of 1 mm to 3 mm and configured to be firmly fixed at an entrance of the left atrial appendage. An indicator 2 is provided at a middle position between two two-way anchoring thorns on the axial support rod 41, or two indicators 2 are respectively provided at roots of the two anchoring thorns on the axial support rod 41, and the indicator 2 is used for accurately positioning under X-ray observation. A metal sleeve 7 is welded in a distal end hub, and the distal end hub and the metal sleeve are provided with a connection member for realizing the connection between the stent and the delivery system, and the connection member may be screw threads 6 and 8, a hole, or a hook, but is not limited to the above means. The stent in a released state has a plum blossom shape and may be stretched and compressed along an axial direction.

The stent 1 for fixing the occluder is formed by laser-cutting a nickel-titanium memory alloy tube. The nickel-titanium alloy tube has an outer diameter of 3.0 mm to 5.0 mm, a wall thickness of 0.15 mm to 0.4 mm and a length of 15 mm to 50 mm, and is hollowed out by laser cutting to form 4 to 8 axial support rods 41, and then is expanded and shaped into a plum blossom shaped stent having an outer diameter of 8 mm to 36 mm by vacuum heat treatment.

The indicator 2 on the stent is formed by winding a platinum, tungsten, platinum alloy wire or gold alloy wire which has a diameter of 0.0508 mm to 0.22 mm on the stent, or by welding a soldering tin which contains platinum, tungsten, platinum alloy or gold alloy on the stent.

Figures 5A, 5B, 5C:
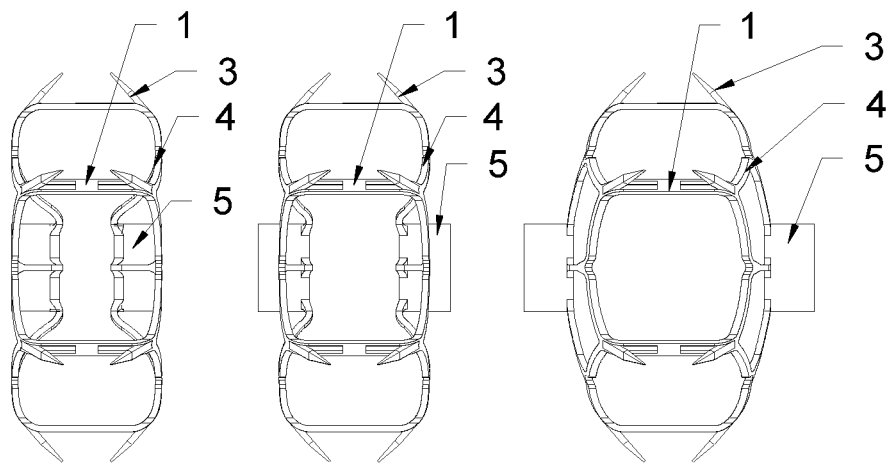
FIGS. 5a, 5b and 5c are schematic views showing the structures of stents according to various embodiments of the present application.

As shown in FIGS. 5a, 5b and 5c, the flexible support rod 4 and the hubs 5 on the stent may have various formation structures. The flexible support rod may be concaved inwardly or protruding outwardly. The hub may be located inside or outside the disk formed by the flexible support rods and may be located at any position with respect to the disk in the axial direction.

Figure 6:
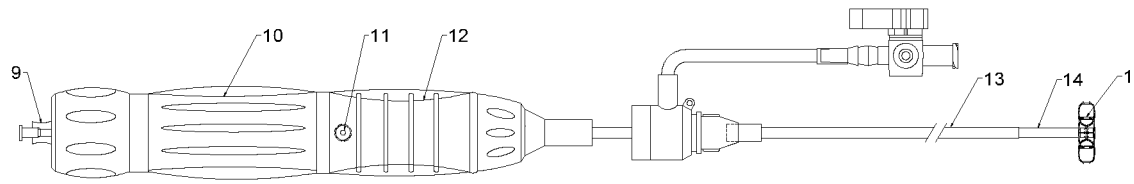
FIG. 6 is a schematic view showing the structure of a delivery system according to an embodiment of the present application.
Figure 7:
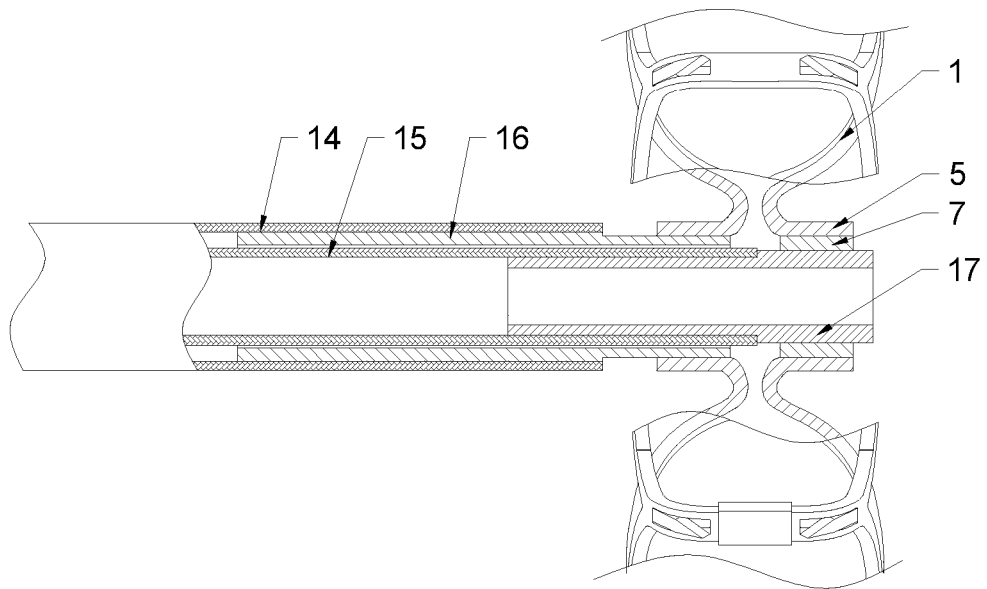
FIG. 7 is a schematic view showing a connection structure between the stent and a catheter of the delivery system according to the embodiment of the present application.

As shown in FIGS. 6 and 7, the stent is positioned at a distal end of the delivery system and connected to the catheters 14, 15 of the delivery system, and the connection between the stent and the catheters may be screw threaded connection as shown in the drawings, but is not limited to this. A metal connector 16 may be provided between the catheter and the hub 5 of the stent, and a metal connector 17 may be provided between the catheter and the metal sleeve 7, and the metal connectors 16 and 17 may be made of stainless steel, nickel-titanium alloy, titanium alloy, platinum or platinum alloy. A device at a proximal end of the delivery system is a grip, and after a distal outer sheath is withdrawn and the stent is delivered, a fixing grip is fixed, and a twist grip is rotated to control the outer catheter 14 and the inner catheter 15 to slide simultaneously by a same displacement in opposite directions, thereby controlling two ends of the stent to gradually change the stent from a stretched state to the original plum blossom shaped state and to fix the stent at the entrance of the left atrial appendage. After the stent is fixed at the entrance of the left atrial appendage, the delivery system and the distal outer sheath are withdrawn, thereby realizing the release of the stent.

Figure 8:
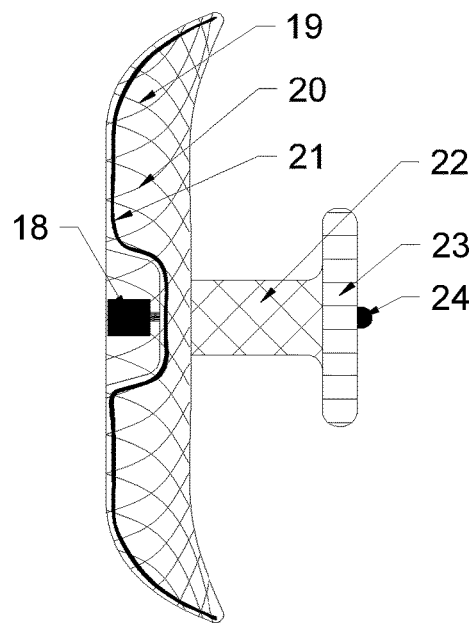
FIG. 8 is a schematic view showing the structure of an occluder according to an embodiment of the present application.

As shown in FIG. 8, the occluder 19 includes a proximal end disk 20, a distal end disk 23 and a waist 22. An end nut 18 is welded at a proximal end of the occluder, and a tip 24 is welded at a distal end of the occluder. A PET or PTFE polymeric membrane 21 is seamed to the proximal end disk with a PET suture. The double-disk occluder may be stretched or compressed into the catheter along the axial direction.

Braid wires, such as a memory alloy wire, a nickel-titanium alloy wire, a titanium wire or a stainless steel wire, are braided and then heat treated to form the occluder, and the braid wire has a diameter of 0.102 mm to 0.305 mm. The occluder is fixed in a mold and shaped to form a double-disk shape by vacuum heat treatment. The proximal end disk of the occluder has a diameter greater than a diameter of the stent by 2 mm to 30 mm, the distal end disk has a diameter of 4 mm to 20 mm, and a length of the waist is same as a width of the stent or a length of the hub 5, and an outer diameter of the waist is 1 mm to 6.0 mm.

Figures 9A, 9B, 9C:
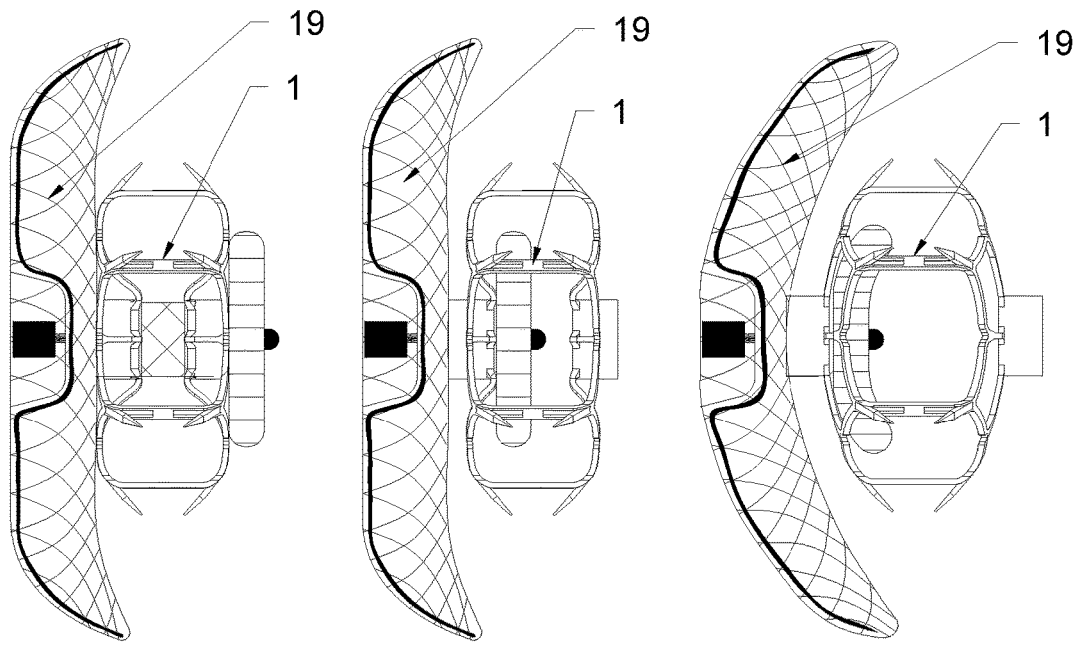
FIGS. 9a, 9b and 9c are schematic views showing the structures of occluders being released to be fixed on the stent according to various embodiments of the present application.
Figure 10:
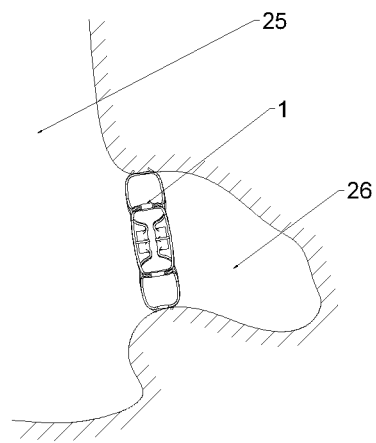
FIG. 10 is a schematic view showing a stent being released to be fixed at an entrance of the left atrial appendage according to an embodiment of the present application.
Figure 11:
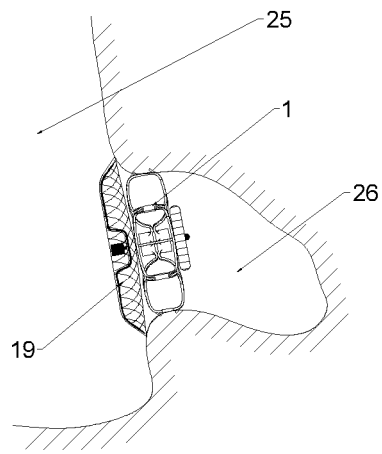
FIG. 11 is a schematic view showing a structure of an embodiment of the present application in which an occluder is released after a stent is released.
Figure 12:
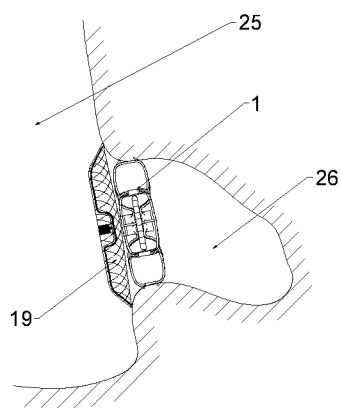
FIG. 12 is a schematic view showing another structure of an embodiment of the present application in which an occluder is released after a stent is released.

As shown in FIGS. 9a, 9b and 9c, the occluder may be released and fixed to the stent, and occluders of various shapes and specifications may be respectively released to stents of various types and specifications. The proximal end disk of the occluder is attached to a proximal end surface of the hub at the proximal end of the stent, and the distal end disk of the occluder is attached to a distal end surface of the hub at the distal end of the stent or a distal end surface of the hub at the proximal end of the stent.

The assembling process is described as follows. The connector 17 on the inner catheter of the delivery system is connected to the metal sleeve 7 on the stent, and the connector 16 on the outer catheter of the delivery system is connected to the hub 5 at the proximal end of the stent. By rotating the grip of the delivery system, the inner catheter and the outer catheter are driven to slide in opposite directions to stretch the stent to a circular tubular shape, thereby accomplishing the assembling process.

In a first embodiment, a stent having a diameter of 15 mm is made from a nickel-titanium alloy tube with an outer diameter of 4.0 mm and a wall thickness of 0.2 mm, and forms a regular hexagonal plum blossom shape after being completely released. An occluder has a proximal end disk having a diameter of 25 mm. A delivery system has an outer diameter of 4 mm and an effective length of 80 cm.

In an animal experiment, a beagle with body weight of about 15 kg is adopted for femoral vein puncture. Under the observation of X-ray, an atrial septum is punctured by an atrial septum puncture needle, a guide wire is delivered into the left atrial appendage along an atrial septum puncture sheath, and then the atrial septum puncture sheath is withdrawn. A 12 F long sheath assembly with a length of 60 cm is delivered into the left atrial appendage along the guide wire and the expansion tube is withdrawn, and the long sheath and the guide wire are remained within the left atrial appendage. The stent system is delivered into the left atrial appendage through the sheath tube along the guide wire until a distal end of the stent coincides with an indicator of the sheath tube, and the distal end of the stent should not exceed the indicator of the sheath tube. The position of the stent is adjusted to allow an indicator of the stent to be located at a center of the entrance of the left atrial appendage, then the sheath tube is withdrawn and the stent is exposed. By twisting the grip, two ends of the stent are driven to move towards the center, thus the stent is expanded, and the two-way anchoring thorns are stabbed into the wall of the atrium at the entrance of the left atrial appendage. When it is confirmed that the stent is fixed firmly, the whole catheter system is twisted reversely to separate the catheters from the stent and withdraw the catheters from the body, and the guide wire is remained. A 6 F sheath tube assembly is delivered into the left atrial appendage along the guide wire until it is determined that an indicator at a distal end of the sheath tube has entered into the stent, then the expansion tube and the guide wire are withdrawn. Then the occlusion system is delivered into the left atrial appendage along the sheath tube, and released onto the stent. When it is determined that the released occluder is fixed firmly, the occluder delivery wire is twisted to be separated from the occluder and is withdrawn from the body together with the sheath tube. Therefore, the operation is accomplished.

A left atrial appendage occlusion device and a delivery system according to the present application are described in detail hereinbefore. The principle and the embodiments of the present application are illustrated herein by specific examples. The above description of examples is only intended to help the understanding of the method and idea of the present application. It should be noted that, for the person skilled in the art, a few of modifications and improvements may be made to the present application without departing from the principle of the present application, and these modifications and improvements are also deemed to fall into the scope of the present application defined by the claims.

The invention claimed is:

1. A left atrial appendage occlusion device, comprising:
    a stent configured to be released and fixed at an entrance of a left atrial appendage to establish an artificial position for fixing an occluder; and
    an occluder configured to be released and fixed to the stent to occlude the left atrial appendage; and
    wherein, the stent comprises a plurality of flexible support rods, and a proximal end hub and a distal end hub, and the proximal end hub and the distal end hub having the same size are located at a center of the stent; the plurality of flexible support rods comprises a plurality of peripheral flexible support rods provided at a periphery of the stent, a plurality of radial flexible support rods transverse to the peripheral flexible support rods, and a plurality of axial flexible support rods; the peripheral flexible support rods form a proximal end disk and a distal end disk which has the same shape and structure, and the proximal end disk and the distal end disk of the stent are respectively connected to the proximal end hub and the distal end hub by the radial flexible support rods, and the proximal end disk and the distal end disk of the stent each forms a regular polygon, and the axial support rods are respectively provided between corresponding vertexes of the regular polygons to connect the proximal end disk and the distal end disk of the stent; and
    wherein the occluder is a double-disk occluder having a proximal end disk configured to be located within a left atrium, a distal end disk configured to be located within the stent or the left atrial appendage, and a waist configured to pass through the proximal end hub.

2. The left atrial appendage occlusion device according to claim 1, wherein,
    the stent is formed by laser-cutting a nickel-titanium alloy tube or heat shaping braided nickel-titanium alloy wires;
    the stent is provided with a plurality of two-way anchoring thorns configured to hook a wall of an atrium at the entrance of the left atrial appendage; and
    a metal sleeve, screw threads, a hole, or a hook is provided on each of the proximal end hub and the distal end hub and is configured to connect the proximal end hub and the distal end hub with a delivery system.

3. The left atrial appendage occlusion device according to claim 2, wherein two ends of each of the axial support rods are both provided with one anchoring thorn, and the anchoring thorn has a length of 1 mm to 3 mm, and has a root arranged on the respective support rod.

4. The left atrial appendage occlusion device according to claim 3, wherein, on the axial support rod, an indicator is provided or not provided at a middle portion between two anchoring thorns or at the root of each anchoring thorn, and the indicator is made of platinum, gold, platinum alloy, tungsten alloy or gold alloy.

5. The left atrial appendage occlusion device according to claim 2, wherein the proximal end hub comprises an inner hole provided with screw threads, a hole, or a hook, and the screw threads, the hole, or the hook is configured to be connected to an outer catheter of the delivery system.

6. The left atrial appendage occlusion device according to claim 5, wherein a metal sleeve is welded in the distal end hub and is made of stainless steel, nickel-titanium alloy, titanium alloy, platinum, or platinum alloy.

7. The left atrial appendage occlusion device according to claim 6, wherein the metal sleeve is provided with screw threads, a hole, or a hook, and the screw threads, the hole, or the hook is configured to be connected to an inner catheter of the delivery system.

8. A delivery system, configured to deliver a left atrial appendage occlusion device, wherein the left atrial appendage occlusion device comprises a stent configured to be released and fixed at an entrance of a left atrial appendage to establish an artificial position for fixing an occluder; and an occluder configured to be released and fixed to the stent to occlude the left atrial appendage; and wherein, the stent comprises a plurality of flexible support rods, and a proximal end hub and a distal end hub, and the proximal end hub and the distal end hub having the same size are located at a center of the stent; the plurality of flexible support rods comprises a plurality of peripheral flexible support rods provided at a periphery of the stent, a plurality of radial flexible support rods transverse to the peripheral flexible support rods, and a plurality of axial flexible support rods; the peripheral flexible support rods form a proximal end disk and a distal end disk which has the same shape and structure, and the proximal end disk and the distal end disk of the stent are respectively connected to the proximal end hub and the distal end hub by the radial flexible support rods, and the proximal end disk and the distal end disk of the stent each forms a regular polygon, and the axial support rods are respectively provided between corresponding vertexes of the regular polygons to connect the proximal end disk and the distal end disk of the stent; and wherein the occluder is a double-disk occluder having a proximal end disk configured to be located within a left atrium, a distal end disk configured to be located within the stent or the left atrial appendage, and a waist configured to pass through the proximal end hub; and wherein the delivery system comprises the stent, the occluder, a distal end outer sheath and a system grip, wherein in a case that the distal end outer sheath is withdrawn and the stent is delivered, the system grip is twisted to control two ends of the stent to retreat to a center of the stent at the same time, or to control two ends of the stent to be stretched outwards at the same time to restore the stent to a retracted state before being released, and the position of the stent is adjusted, then the stent is released again till the stent is accurately fixed at the entrance of the left atrial appendage.

9. The delivery system according to claim 8, wherein the distal end outer sheath is provided on the delivery system or is provided separately, and the distal end outer sheath is slidably connected to the stent.

10. The delivery system according to claim 9, wherein the delivery system is provided with an outer catheter and an inner catheter which are coaxial and are slidable with respect to one another.

11. The delivery system according to claim 10, wherein the outer catheter has a distal end connected to the proximal end hub of the stent, and a connector is provided between the outer catheter and the proximal end hub.

12. The delivery system according to claim 10, wherein a metal sleeve is welded in the distal end hub and is made of stainless steel, nickel-titanium alloy, titanium alloy, platinum, or platinum alloy; and the inner catheter has a distal end connected to the metal sleeve on the distal end hub of the stent, and a connector is provided between the inner catheter and the metal sleeve.

13. The delivery system according to claim 8, wherein the waist of the occluder is configured to pass through the proximal end hub or pass through the proximal end hub and the metal sleeve at the same time.

14. The delivery system according to claim 13, wherein a polymeric membrane made of polyethylene terephthalate or polytetrafluoroethylene is provided inside the proximal end disk of the occluder.

15. The delivery system according to claim 14, wherein a diameter of the proximal end disk of the occluder is greater than a diameter of the stent by 2 mm to 30 mm, and the distal end disk of the occluder has a diameter of 4 mm to 20 mm.

16. The delivery system according to claim 8, wherein,
the stent is formed by laser-cutting a nickel-titanium alloy tube or heat shaping braided nickel-titanium alloy wires;
the stent is provided with a plurality of two-way anchoring thorns configured to hook a wall of an atrium at the entrance of the left atrial appendage;
and a metal sleeve, screw threads, a hole, or a hook is provided on each of the proximal end hub and the distal end hub and is configured to connect the proximal end hub and the distal end hub with the delivery system.

* * * * *